US010420899B2

(12) United States Patent
Draper et al.

(10) Patent No.: US 10,420,899 B2
(45) Date of Patent: Sep. 24, 2019

(54) ASSEMBLY FOR A DRUG DELIVERY DEVICE

(71) Applicant: Sanofi, Paris (FR)

(72) Inventors: Paul Richard Draper, Worcestershire (GB); Michael Bainton, Warwickshire (GB); Matthew Jones, Warwickshire (GB)

(73) Assignee: Sanofi, Paris (FR)

( * ) Notice: Subject to any disclaimer, the term of this patent is extended or adjusted under 35 U.S.C. 154(b) by 127 days.

(21) Appl. No.: 15/128,376

(22) PCT Filed: Mar. 23, 2015

(86) PCT No.: PCT/EP2015/056034
§ 371 (c)(1),
(2) Date: Sep. 22, 2016

(87) PCT Pub. No.: WO2015/144606
PCT Pub. Date: Oct. 1, 2015

(65) Prior Publication Data
US 2017/0106145 A1     Apr. 20, 2017

(30) Foreign Application Priority Data

Mar. 26, 2014   (EP) ..................... 14305434

(51) Int. Cl.
*A61M 5/32* (2006.01)
*A61M 5/20* (2006.01)
*A61M 5/34* (2006.01)

(52) U.S. Cl.
CPC ............ *A61M 5/3202* (2013.01); *A61M 5/20* (2013.01); *A61M 5/34* (2013.01); *A61M 2205/14* (2013.01)

(58) Field of Classification Search
CPC .......... A61M 5/20; A61M 5/34; A61M 5/343; A61M 5/3202; A61M 2205/14; A61M 2205/2073
See application file for complete search history.

(56) References Cited

U.S. PATENT DOCUMENTS

| 2003/0105430 | A1* | 6/2003 | Lavi | .................... | A61M 5/2033 |
| | | | | | 604/136 |
| 2013/0172819 | A1* | 7/2013 | Iio | ........................... | A61M 5/20 |
| | | | | | 604/111 |

(Continued)

FOREIGN PATENT DOCUMENTS

| CN | 102256644 | 11/2011 |
| CN | 103228304 | 7/2013 |

(Continued)

OTHER PUBLICATIONS

Information Disclosure Statement and Written Opinion in International Application No. PCT/EP2015/056034, dated Jun. 19, 2015, 10 pages.

(Continued)

*Primary Examiner* — Bhisma Mehta
*Assistant Examiner* — James D Ponton
(74) *Attorney, Agent, or Firm* — Fish & Richardson P.C.

(57) ABSTRACT

An assembly for a drug delivery device (200) is provided, the assembly comprising a needle mounting feature (1), a needle detector (2), a housing (3) and a movable feature (4) which is movably connected to the housing (3) and movable with respect thereto between a first position and a second position different from the first position. The needle detector (2) is configured to detect whether a needle (101) is mounted to the needle mounting feature (1). The assembly is further configured such that when a needle (101) is mounted to the needle mounting feature (1), the movable feature (4) is in the (Continued)

second position and when the needle (101) is not mounted to the needle mounting feature (1), the movable feature (4) is in the first position.

18 Claims, 7 Drawing Sheets

(56) References Cited

U.S. PATENT DOCUMENTS

| | | | | |
|---|---|---|---|---|
| 2014/0107585 A1* | 4/2014 | Eggert | ................ | A61M 5/3202 |
| | | | | 604/193 |
| 2015/0182706 A1* | 7/2015 | Wurmbauer | ............ | A61M 5/34 |
| | | | | 604/111 |

FOREIGN PATENT DOCUMENTS

| | | |
|---|---|---|
| CN | 103648561 | 3/2014 |
| EP | 2361647 | 8/2011 |
| EP | 2641626 | 9/2013 |
| EP | 2674184 | 12/2013 |
| JP | 2013-188519 | 9/2013 |
| WO | WO 2005/077441 | 8/2005 |
| WO | WO 2013/186618 | 12/2013 |
| WO | WO 2012/066767 | 5/2014 |

OTHER PUBLICATIONS

International Preliminary Report on Patentability in International Application No. PCT/EP2015/056034, dated Sep. 27, 2016, 8 pages.

* cited by examiner

ASSEMBLY FOR A DRUG DELIVERY DEVICE

CROSS-REFERENCE TO RELATED APPLICATIONS

This application is a U.S. national stage application under 35 USC § 371 of International Application No. PCT/EP2015/056034, filed on Mar. 23, 2015, which claims priority to European Patent Application No. 14305434.4 filed on Mar. 26, 2014, the entire contents of which are incorporated herein by reference.

The present disclosure relates to an assembly for a drug delivery device, such as an injector-type device, and to the drug delivery device.

Some aspects of the present disclosure can be implemented to provide an assembly by which a drug delivery device can be improved.

The assembly relates to drug delivery devices that can be operated to deliver a number of user variable doses of medicament from a cartridge via a needle. Preferably, the assembly relates to semi-automatic or automatically driven drug delivery devices.

Some aspects can be implemented by the subject-matter of the independent claim. Advantageous embodiments and refinements are subject-matter of the dependent claims.

One aspect of the present disclosure relates to an assembly for a drug delivery device comprising a needle mounting feature, a needle detector, a housing and a movable feature which is movable with respect to the housing between a first position and a second position being different from the first position. Furthermore, the needle detector is configured to detect whether a needle is mounted to the needle mounting feature. The assembly is configured such that when a needle or a needle unit is mounted to the needle mounting feature, the movable feature is in the second position and, when the needle is not mounted to the needle mounting feature, the movable feature is in the first position.

A further aspect relates to the drug delivery device. In an embodiment, the drug delivery device comprises the assembly. Particularly, the drug delivery device can be embodied compactly if the assembly is applied to the drug delivery device.

The configuration of the assembly advantageously allows to define two states of the assembly and/or the drug delivery device depending on whether a needle or a needle unit is mounted to the needle mounting feature or not.

In an embodiment, the housing of the assembly is a housing of the drug delivery device.

In an embodiment, the assembly is configured such that, during mounting of the needle to the needle mounting feature, the movable feature is moved from the first position to the second position. This embodiment allows an instantaneous change of the state of the assembly and/or the drug delivery device during mounting of the needle to the needle mounting feature.

In an advantageous embodiment, in the second position of the movable feature, the movable feature protrudes from an outer surface of the housing. In the first position, the movable feature protrudes less from an outer surface of the housing than the movable feature does in its second position. Preferably, the movable feature does not protrude at all from the outer surface of the housing in the first position. According to this embodiment, the states of the assembly and/or the drug delivery device pertaining to an attached or detached needle or needle unit can be defined in that the movable feature protrudes from the outer surface of the housing or not. Thereby, further mechanisms or actions may be applied to the assembly, depending on whether a needle or needle unit is mounted to the needle mounting feature or not. For instance, further components, such as a cap, may mechanically interact with the movable feature.

In an embodiment, the needle detector is movable with respect to the housing. The assembly is configured such that the needle detector triggers movement of the movable feature. This may be carried out by any suitable measures.

In an embodiment, the assembly is configured such that the movement of the needle detector is converted into the movement of the movable feature. Preferably, said conversion is carried out mechanically. In this way, it is easily achieved that, by the movement of the needle detector, also the movable feature is moved such that it may protrude from the outer surface of the housing. The needle detector may comprise a movable member, e.g., a pin which is pushed inside the housing when the needle or the needle unit is mounted to the needle mounting feature. Said pin may be mechanically coupled to the movable feature.

In an embodiment, the needle detector is movable in an axial direction and the movement of the movable feature takes place radially with respect to the axial direction. This embodiment may allow a mechanical interaction of further components or mechanisms of the assembly or the device with the movable feature in an expedient way. Said mechanisms or components, preferably, relate to the attachment or detachment of a cap, such as a protective cap, to the assembly, particularly to the housing, or to the drug delivery device.

In an embodiment, the movement of the movable feature is directed radially with respect to a longitudinal axis of the assembly.

In an embodiment, the movable feature is biased towards the first position of the movable feature. According to this embodiment, it may be achieved that, unless a needle or needle unit is mounted or secured to the needle mounting feature, the movable feature is in the first position and does not protrude from the outer surface of the housing. Particularly, a ground state of the movable feature may, thereby, expediently be defined.

In an embodiment, the assembly comprises a needle unit with a needle, wherein the needle is fixable or fixed to the needle unit. The needle unit is mountable to the needle mounting feature, and wherein the needle detector is configured to interact with the needle unit during mounting of the needle unit to the needle mounting feature, whereby the needle detector can detect whether the needle unit is mounted to the needle mounting feature. According to this embodiment, the movable feature is in the first position when the needle unit is not mounted to the needle mounting feature and when the needle unit is mounted to the needle mounting feature, the movable feature is in the second position.

In an embodiment, the needle mounting feature is arranged at or in recessed area of the housing. The recessed area is, preferably, spaced from a distal end of the housing. According to this embodiment, the length of the assembly or the device including the needle or the needle unit can advantageously be reduced, as compared to a situation in which the needle or needle unit is mounted at the very distal end or end face of the assembly or the drug delivery device.

In an embodiment, the housing is configured to house or retain a drive mechanism for dispensing a drug and a cartridge for retaining the drug. The housing may also house or retain further components of the drug delivery device.

In an embodiment, the assembly comprises a cap which is configured such that in the first position of the movable feature, the cap is securable to the assembly in a first mounting position and in the second position of the movable feature, the cap is securable to the assembly in a second mounting position being different from the first mounting position. Depending on the attachment of the needle or the needle unit to the housing, the cap can thus be secured to the assembly either in the first or in the second mounting position.

In an embodiment of the drug delivery device, the cap is secured to the assembly either in the first or in the second mounting position. Preferably, the cap covers the needle mounting feature and the needle detector. As an advantage, the needle mounting feature and the needle detector and/or the needle or needle unit can be protected by the cap from external influences. In an embodiment of the drug delivery device, when the cap is secured in the first mounting position, the drug delivery device comprises a first length and, when the cap is secured in the second mounting position, the drug delivery device comprises a second length, wherein the second length is greater than the first length. Preferably, the cap is securable to the housing of the assembly. Preferably, the cap is further configured to interact with the movable feature during securing of the cap to the assembly.

As an advantage, the device length can be kept small when the cap is secured to the assembly in the first mounting position, as compared to the situation, wherein the cap is secured to the assembly in the second mounting position.

In an embodiment of the drug delivery device, in the first position of the movable feature, the movable feature prevents the cap from being secured to the assembly in the second mounting position. Particularly, the protrusion of the movable feature from the outer surface of the housing of the assembly prevents the cap from being secured in the second mounting position. The cap is, expediently configured accordingly.

In an embodiment of the drug delivery device, when the cap is secured in the second mounting position, a dose indicator of the drug delivery device is visible for a user. When the cap is secured to the assembly in the second mounting position, the dose indicator is not visible for the user. According to this embodiment, the user may be informed about a state, e.g. a dose state, of the drug delivery device by the visibility of the dose indicator. When the dose indicator is visible for the user, the user may further be informed that the drug delivery device is possibly currently in use or in a primed or filled state, as a needle or needle unit is mounted to the assembly. This is because when the cap is secured to the assembly in the second mounting position it may be indicated to the user that a needle or needle unit is actually mounted to the assembly.

The difference in device length between the different states of the drug delivery device, i.e. in which the cap is secured in the first and in the second mounting position may relate to, e.g. an axial length of the device by which the device length is or has to be increased due to the mounting of a needle or needle unit to the assembly or the device.

In an embodiment of the drug delivery device, the drug delivery device comprises a drive mechanism for dispensing a drug and a cartridge retaining the drug.

The term "drug" or "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments, may also apply for other aspects and embodiments. Further features and advantageous aspects of the subject matter of the disclosure will become apparent from the following description of the exemplary embodiment in conjunction with the figures, in which.

Figure 1:
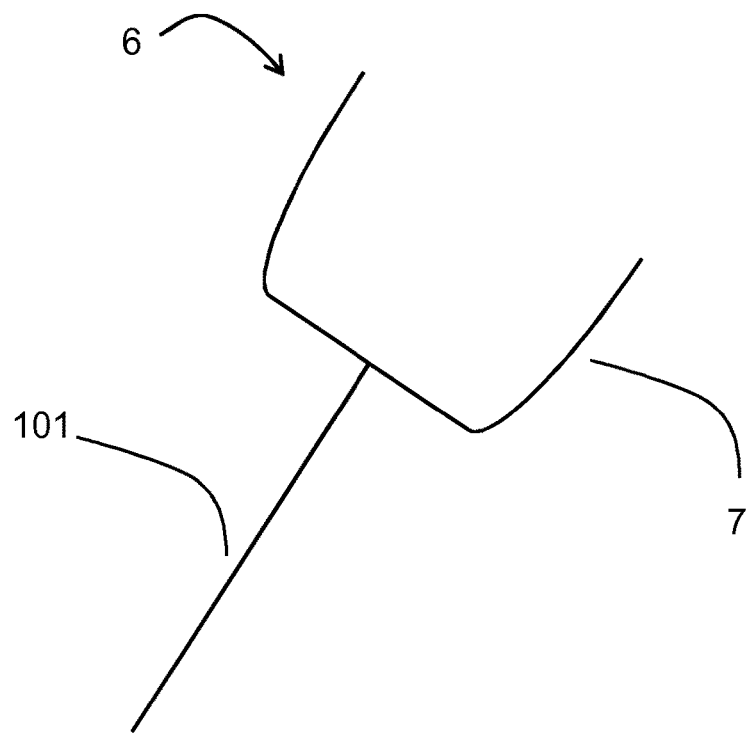
FIG. 1 shows a simplified schematic view of a needle unit.

Like elements, elements of the same kind and identically acting elements may be provided with the same reference numerals in the figures. Additionally, the figures may be not true to scale. Rather, certain features may be depicted in an exaggerated fashion for better illustration of important principles.

FIG. 1 shows a simplified schematic view of a needle unit 6. The needle unit 6 comprises a needle hub 7. The needle unit 6 further comprises a needle 101. The needle 101 is fixable or fixed to the needle hub 7. The needle unit 6, particularly the needle hub 7 is configured to be mountable to a needle mounting feature (cf. assembly of FIG. 2). The needle is configured to pierce through a membrane of a cartridge to establish fluid communication between the interior of the cartridge and the exterior of the cartridge.

Figure 2:
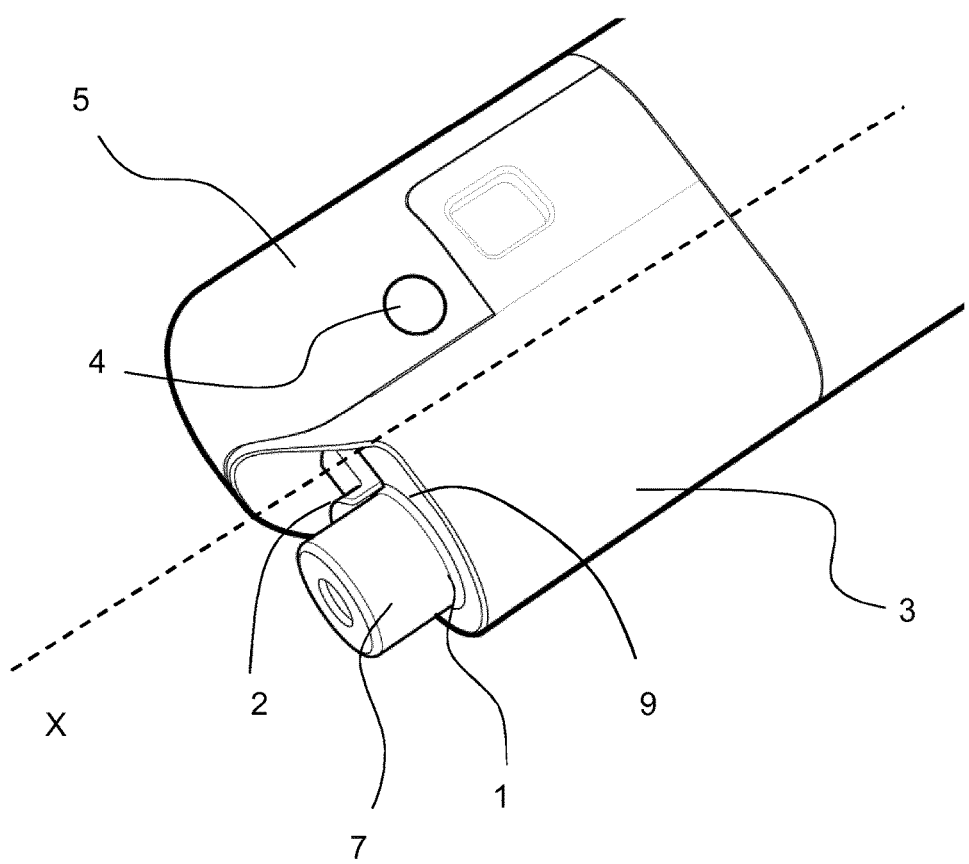
FIG. 2 shows a perspective view of parts of an embodiment of an assembly.
Figure 3:
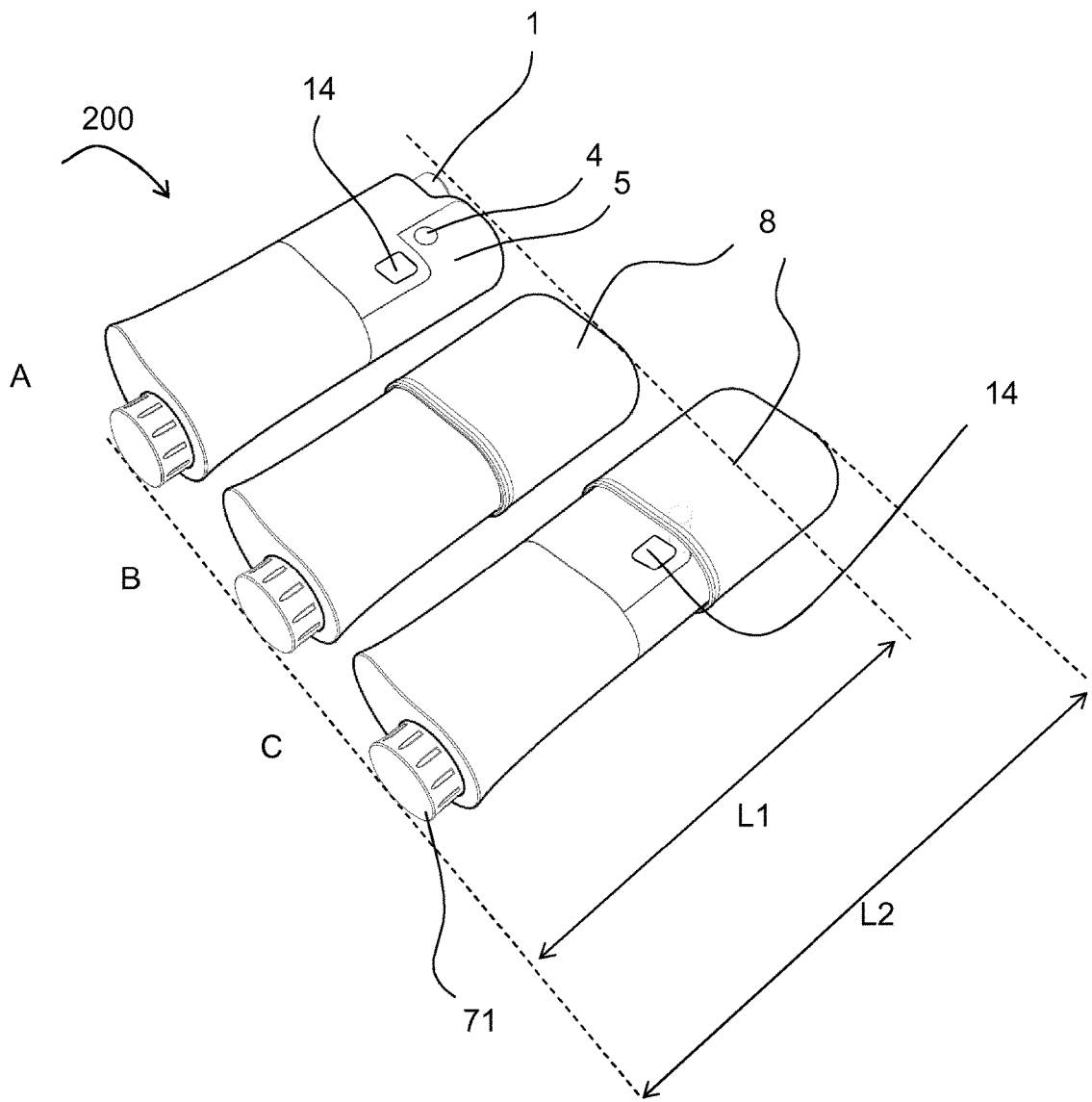
FIGS. 3A to 3C show perspective views of the assembly applied in a drug delivery device in different states.

FIG. 2 shows parts of an assembly for a drug delivery device (see reference numeral 200 in FIGS. 3 and 4) and/or parts of the drug delivery device. Particularly, a distal end of the assembly or parts thereof are shown. The distal end opposes a proximal end of the assembly or the drug delivery device 200 (not shown in FIG. 2). Preferably, a longitudinal axis X of the assembly or the device 200 runs through the distal as well as the proximal end.

The "distal end" of the assembly or the drug delivery device or a component thereof shall mean the end which is closest to the dispensing end of the assembly or the drug delivery device.

The "proximal end" of the assembly or the drug delivery device or a component thereof shall mean the end which is furthest away from the dispensing end of the assembly or the drug delivery device.

The assembly comprises a housing 3. The housing 3 comprises an outer surface 5. The housing 3 has a slight oval or elongate cross section. The assembly further comprises a needle mounting feature 1. The needle mounting feature 1 is disposed at said distal end. The needle mounting feature 1 is preferably provided by a cartridge or cartridge holder (cf. reference numeral 20 in FIG. 4) of the assembly or the drug delivery device 200. The assembly further comprises a needle detector 2. The needle detector 2 is arranged at an inner side the needle mounting feature 1 in a distal cut-out or recessed area 9 (not explicitly indicated) of the housing 3. The recessed area 9 is spaced from a distal end of the housing. The needle mounting feature 1 is, preferably, also arranged at the recessed area 9.

The needle detector 2 may comprise or constitute an axially movable member, e.g. a pin. The assembly further comprises a movable feature 4 which is slightly spaced from the needle detector 2. The movable feature 4 is configured movable, particularly in the radial direction with respect to the housing 3 between a first position and a second position.

The needle detector 2 is configured to detect whether the needle 101 or needle unit 6 is mounted to the needle mounting feature 1. The assembly is further configured such that when the needle 101 or needle unit 6 is not mounted to the needle mounting feature 1, the movable feature 4 is in the first position and, when the needle 101 or needle unit 6 is mounted to the needle mounting feature 1, the movable feature 4 is in the second position.

During mounting of the needle 101 or needle unit 6 to the needle mounting feature 1, the movable feature 4 is moved from the first position to the second position.

When the needle unit 6 is mounted to the needle mounting feature 1, the needle hub 7 is preferably pushed over the needle mounting feature 1 and snap-fitted or otherwise axially fixed to the needle mounting feature 1. Therefore, the needle hub 7 may be shaped to receive the needle mounting feature 1 or vice versa. For the sake of fixation, the needle hub 7 may further be configured to engage a hook or collar of the needle mounting feature 1. During mounting of the needle unit 6, the needle hub 7, preferably, displaces or moves the needle detector 2 in the proximal direction, after the needle unit 6 has been put over the needle mounting feature 1. Furthermore, the movable feature 4 is, preferably, biased towards the first position, e.g. by a biasing spring which tends to move the needle detector 2 in the distal direction and thereby defines an initial or ground state of the needle detector 2. When the needle unit 6 is mounted and engaged to the needle mounting feature 1, the needle detector 2 is, preferably held in its proximal most position against the resilience of the biasing.

The movement of the needle detector 2 is, preferably, converted into the movement of the movable feature 4. The movable feature 4 is, preferably, movable in a direction aligned perpendicular to the direction of movement of the needle detector 2. Preferably, the movable feature 4 is radially movable between the first and the second position. The movable feature may be guidable or guided between the first and the second position. Said radial movement may extend in a direction perpendicular to the longitudinal axis X.

For the mentioned conversion of movement, the movable feature 4 is mechanically coupled to the needle detector 2. For instance, a part of the needle detector 2 may engage an obliquely oriented face (not explicitly indicated) of the movable feature 4 such that, when the needle detector 2 is moved proximally, said movement is converted into the radial movement of the movable feature 4.

When the movable feature 4 is in the first position, it does preferably not or not significantly protrude or protrudes less from the outer surface 5 of the housing 3 than the movable feature does when it is in its second position. When the movable feature is in the second position, it expediently protrudes from the outer surface 5 of the housing 3. In this way, the movable feature may act as a stop or fixation element for a cap of the device (see below), for example.

FIG. 3A shows a perspective view of the drug delivery device 200 comprising the assembly. As compared to FIG. 2, the device 200 is shown turned upside down. The housing 3 of the assembly may be or constitute a housing of a drug delivery device 200 (see also FIG. 4). The housing 3 comprises a dose indicator (not explicitly indicated). The dose indicator may be or comprise a window 14 through which a selected or dispensed dose of drug may be indicated to the user, e.g. during an operation of the assembly or the drug delivery device 200. The device 200 further comprises a dial grip 71, e.g. for setting or dialing a dose of drug (see FIG. 3C and description below).

The assembly further comprises a cap 8. FIG. 3B shows the drug delivery device 200, wherein no needle unit is mounted to the needle mounting feature. However, the cap 8 is secured to the housing such that the cap 8 covers at least a distal section of the outer surface 5, the needle mounting feature 1, the needle detector 2 (not shown in FIG. 3A), the movable feature 4, as well as the window 14.

In FIG. 3B, the cap is secured to the assembly in a first mounting position. During the securing, the cap 8 is preferably pulled over the distal end of the assembly or the device 200. Thereby, the cap does, expediently, not interact with the movable feature 4, as the movable feature 4 is in the first position. In the second mounting position, the cap is—instead—preferably fixed or secured to the housing 3 by suitable securing or fixation elements (not explicitly indicated) of the cap and/or the housing, such as e.g. a snap and/or frictional engagement. To this effect, the housing 3 and or the cap 8 may be provided with the corresponding fixation elements. When the cap 8 is secured to the assembly in the second mounting position a device length L2 is defined.

In FIG. 3C, the needle unit 6 is mounted to the needle mounting feature (not explicitly shown) and the drug delivery device 200 is shown with the cap 8 being secured in a second mounting position. When the cap is secured to the assembly in the second mounting position, the cap 8 preferably mechanically interacts with the movable feature 4 such that the cap 8 can thereby be secured to the assembly. To this effect, the movable feature, preferably, rigidly protrudes from the outer surface 5, when the needle unit 6 is mounted to the needle mounting feature 1, i.e. that the movable feature 4 is rigidly held in the second position, as explained above. This may be facilitated by a corresponding rigid engagement or securement of the needle unit 6 to the needle mounting feature 1, such that—due to the mechanical coupling of the movable feature 4 and the needle detector 2—the movable feature 4 is sufficiently urged or held in the second position, so as to serve for a fixation element for the cap 8. For said fixation, the cap 8 may, e.g. comprise a recess (not shown) for receiving the part of the movable feature 4 protruding from or beyond the outer surface 5.

Alternatively, the cap 8 may only abut the movable feature 4, e.g. as a stop, wherein the cap 8 may then be secured to the housing 3 by further securing or fixation elements of the cap and/or the housing or not secured at all. Then, the movable feature 4 may act as a limitation feature for the cap limiting the extent to which the cap can e.g. be put over the needle mounting feature 1.

The above-mentioned fixation elements of the housing are, preferably, different or axially spaced from the further fixation elements of the housing.

When the cap 8 is secured to the assembly in the first mounting position, a device length L1 is defined which is less than the length L2. Expediently, due to the fixation of the needle unit 6, the movable feature 4, prevents the cap 8 from being pulled further over the distal end of the housing towards the second mounting position.

When the cap is secured to the assembly in the second mounting position, the window 14, and thereby a dose indication, is further still visible for the user.

The assembly of the drug delivery device 200 further comprises a dial grip 71 by which a user of the drug delivery device 200 may set and/or dispense a dose of drug. This is particularly expedient when the assembly is applied to devices, wherein user-settable or -variable doses of drug can be dispensed.

As an alternative to the above exemplary description, the needle detector may also be coupled to the movable feature by means different from mechanical ones. For example, the needle detector may be moved during mounting of a needle or needle unit to the needle mounting feature, thereby activating an electronic switch or detector unit which, in turn, triggers the detection of the needle unit by the needle detector. Consequently, an activation or movement of the movable member from the first to the second position may be caused electronically, electro-mechanically or optically.

The needle detector is, furthermore, not restricted to mechanical means. For example, the needle detector may be an optical sensor, e.g. comprising a light beam or a proximity sensor, for example.

Figure 4:
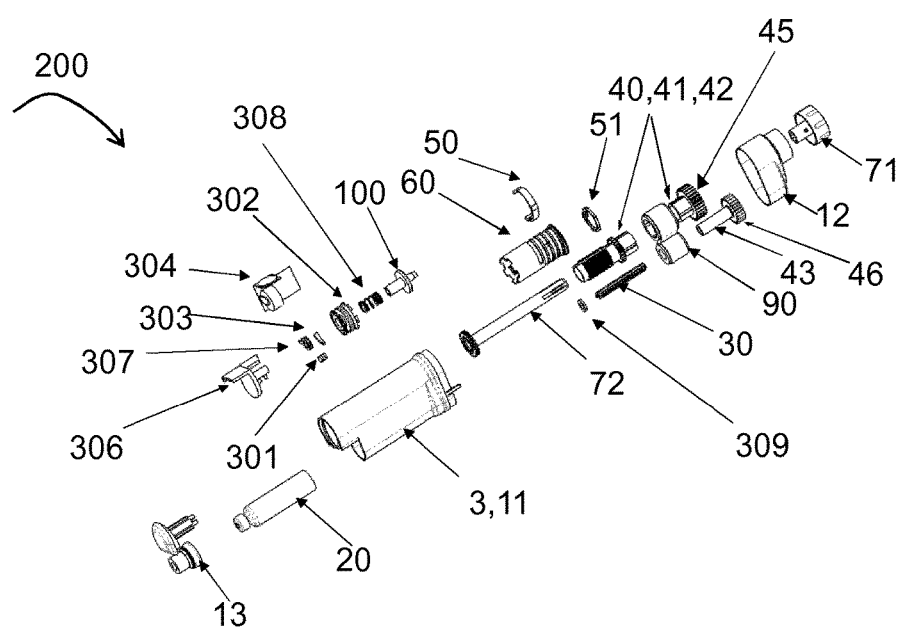
FIG. 4 shows an exploded view of components of the drug delivery device.

FIG. 4 shows the component parts of the drug delivery device 200 in an exploded perspective view. The device 200 has a distal end (left end) and a proximal end (right end). The drug delivery device 200 comprises a housing 3, a cartridge 20, a piston rod or lead screw 30, a drive mechanism 40, a dose nut 50, a dial sleeve 60, the dial grip 71, a tubular element 72, a power reservoir 90, such as a motor spring, and a clicker 100.

According to the present application, in order to decrease the size of the device, the cartridge 20 has preferably an increased cartridge diameter, e.g. as compared to a conventional cartridge and/or device, whereby it may be enabled that the length of the device is reduced whilst maintaining the equivalent total medicinal dose.

The housing 3 or body of the device 200 comprises a main housing 11, a proximal housing 12 and a distal housing or cartridge holder 13. The main housing 11 is a generally tubular element with an oblong cross section. The window 14 or aperture is provided in the main housing 11. The main housing 11, the proximal housing 12 and the cartridge holder 13 can be plugged or snapped together during assembly to close both open ends of the main housing 11. Further, the housing components may be glued or welded together to form a rigid and permanently attached housing unit. The cartridge holder 13 may have a distal aperture in its upper region, which may have an outer thread or lug or the like for attachment of the needle unit 6 (not shown in FIG. 4).

The housing provides location for the medicament cartridge 20, which is held in the upper part (as seen in FIG. 4) of the main housing 11 and the cartridge holder 13.

The main housing 11 has an inner wall with a threaded section (not explicitly indicated) engaging piston rod 30. The cartridge 20 is a glass ampoule with a movable bung (not explicitly indicated) located in its proximal aperture.

The lead screw 30 is an elongate member with an outer thread (not explicitly indicated) which is rotationally constrained to the drive mechanism 40 via a splined interface. The interface comprises at least one longitudinal groove or track (not explicitly indicated) and a corresponding protrusion or spline(s) 44 (cf. FIG. 7) of the drive mechanism 40. When the drive mechanism 40 is rotated, the lead screw 30 is forced to move axially relative to the drive mechanism 40, through its threaded interface with the housing 3. The distal end of the piston rod 30 is provided with a bearing 309 which may abut the cartridge bung.

The drive mechanism 40 comprises a drive sleeve, which has for manufacturing reasons a drive sleeve lower part 41 and a drive sleeve upper part 42, and a drive tube 43. The drive sleeve lower part 41 and the drive sleeve upper part 42 are rigidly connected to form a unit when in use. The drive tube 43 is arranged on a first longitudinal axis (not explicitly indicated) and the drive sleeve is arranged on a second longitudinal axis (not explicitly indicated), which is at least approximately parallel to and spaced from the first longitudinal axis.

On the inside of the drive tube 43, splines (not explicitly indicated) are provided engaging corresponding grooves (not explicitly indicated) of the piston rod 30. The drive tube 43 surrounds the piston rod 30 which is axially displaceable relative to the drive tube 43.

Preferably, the device 200 is a disposable spring-powered pen injector. It has low torque requirements to set a dose since the power reservoir 90, which may be a motor spring, is pre-charged, low force requirements to trigger dispense of medicament and permits any dose to be selected within a range of zero to a pre-defined maximum.

The device 200 further comprises a dose indication mechanism. The dose indication mechanism comprises an optical encoder 301, an encoder disk 302, a dial switch 303, a dose assembly 304, the clicker 100, a carrier 306, mode contacts 307 and a trigger spring 308. The dose indication mechanism may further comprise a battery and/or a sounder or beeper. The dose indication mechanism may provide the advantage of a large display (compare dose assembly 304 in FIGS. 5A, 5B and 6) and the capability of alerting the user to the end of dose and end of a dwell time period via the sounder and/or the display. The device 200 may additionally have a memory function and record the dose quantity and dosing times which may be downloadable to a PC or a comparable device. Due to the provision of the dose indication mechanism the device can be embodied compactly such as smaller than a device comprising e.g. a mechanical dose indicator. Particularly, the electronic display also removes the requirement for large printed numbers on a mechanism component, which means that components can be embodied smaller.

Figure 5A:
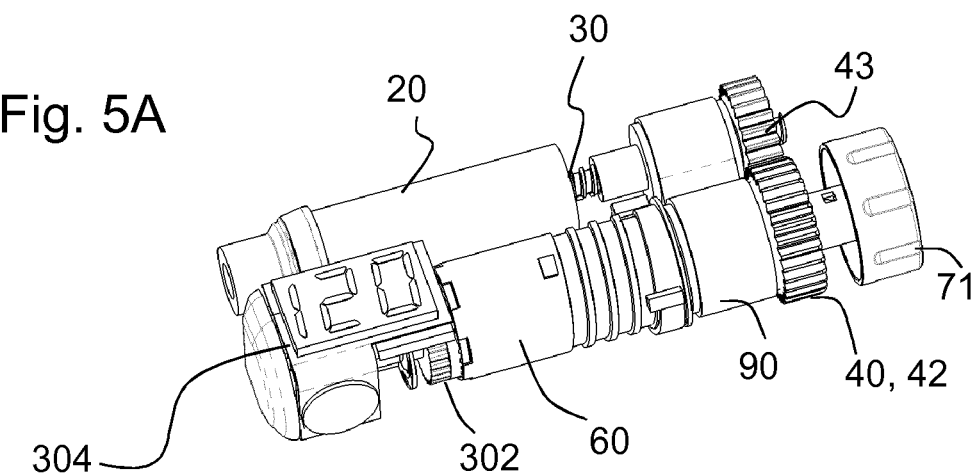
FIG. 5A shows a perspective view of sub-assembled components of the drug delivery device including a dose indication mechanism.
Figure 5B:
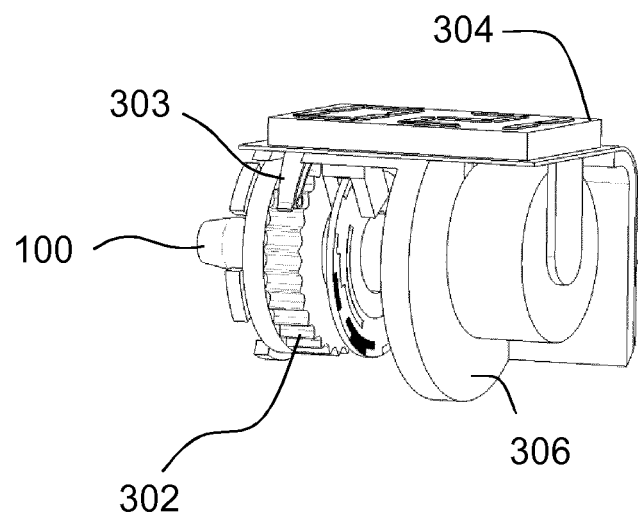
FIG. 5B shows at least parts of the dose indication mechanism in a perspective view.
Figure 6:
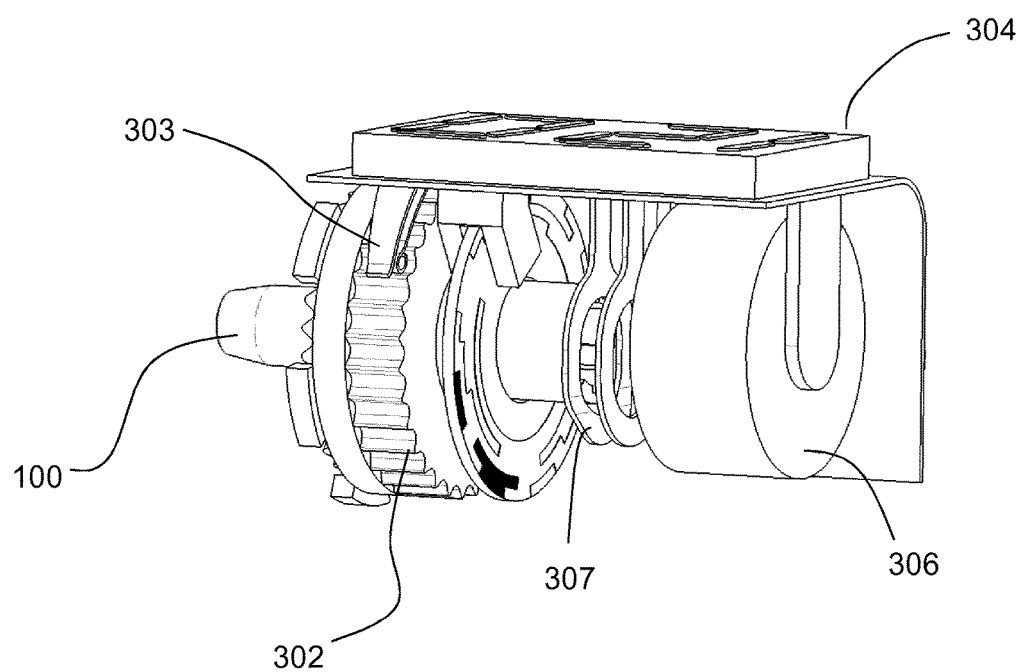
FIG. 6 shows an alternative embodiment of parts of the dose indication mechanism in a perspective view.

In the FIGS. 5A, 5B and 6, components of the dose indication mechanism are shown in greater detail.

For setting a dose, rotation of the dial grip 71 causes the dial sleeve 60 to rotate and the dose nut 50 to travel between a zero dose abutment stop and a maximum dose abutment stop (not explicitly indicated) on the dial sleeve 60. The maximum dose abutment stop may relate to e.g. 120 units of drug. The torque applied by the user to the dial grip 71 during setting, is reacted via the dial sleeve 60 and the dose nut 50 back to the housing 3 when the mentioned abutments are engaged. There is an axial toothed interface between the clicker 100 and the tubular element 72 which are forced together by the trigger spring 308 which generates discrete dose positions and tactile and/or audible feedback to the user. The drive mechanism 40 is rotationally restrained during dialing or setting via a splined interface to the housing 3. Rotation of the dial sleeve 60 also causes rotation of the encoder disk 302 which allows the dose assembly 304 to ascertain the value of the dialed dose via the optical encoder 301. The dose assembly 304 may e.g. be a printed circuit board assembly (PCBA). The encoder disk 302 may comprise a 5-bit absolute gray code, which allows absolute encoding of e.g. 32 units of drug dialed per revolution and incremental counting of the total number of revolutions dialed and hence the total dose dialed or set. The encoder disk 302 also contains radial teeth that correspond to each dialed unit of medicament. These energise the dial switch 303 as each unit is dialed and can be used as a system "wake-up" to alert the dose assembly 304 to turn on the optical encoder 301. This enables that battery life can be maximised since, as soon as dialing stops, the optical encoder 301 can return to its "sleep" mode.

Figure 7:
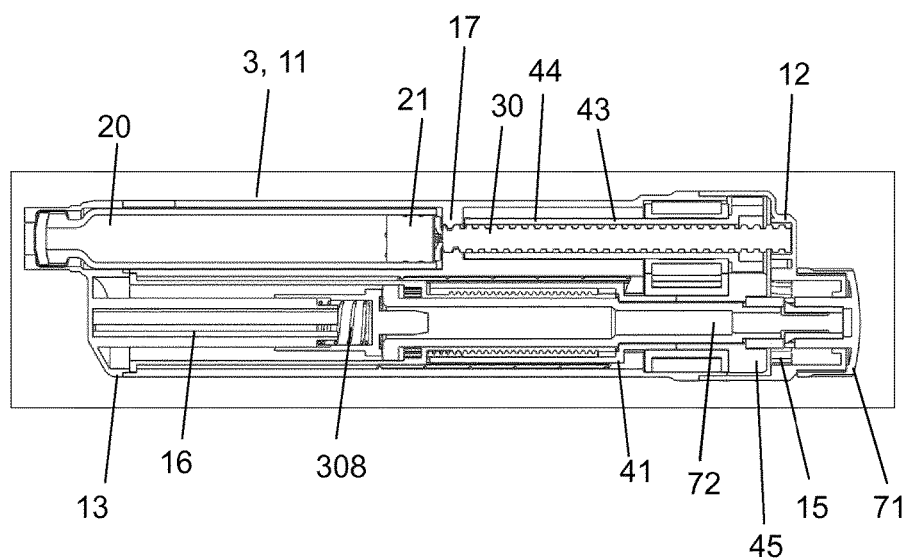
FIG. 7 shows an exemplary sectional view of the device of FIG. 4.

In the sectional exemplary view of FIG. 7, it is shown that on the inside of the drive tube 43, the splines 44 are provided engaging corresponding grooves of the piston rod 30. The dose indication mechanism as described above is—for simplicity reasons—not shown in FIG. 7. It is shown that the drive tube 43 surrounds the piston rod 30 which is axially displaceable relative to the drive tube 43. As shown in FIGS. 4 and 7, the drive sleeve upper part 42 and the drive tube 43 may each have—at their proximal end—a pinion 45, 46, which mesh such that rotation of the drive sleeve 41, 42, is transmitted to the drive tube 43. The drive sleeve 41, 42, is axially movable between a proximal position (during dose setting and/or correcting of a dose) in which pinion 45 further engages teeth 15 of the housing 10, and a distal position (dose dispensing position, see FIG. 7) in which the pinion 45 is disengaged from the teeth 15. However, in both axial positions pinions 45, 46 remain in at least partial engagement.

The dial grip 71 abuts the drive sleeve 41, 42, such that axial movement of the dial grip 71 in the distal direction entrains the drive sleeve 41, 42, and axial movement of the drive sleeve 41, 42, in the proximal direction entrains the dial grip 71.

The trigger spring 308 may be a compression spring being located on a splined pin 16 and inside the clicker 100 urging the clicker 100 in the proximal direction. The trigger spring 308 may be arranged to push the drive sleeve 41, 42 in the proximal direction, whereas a user may overcome the trigger spring force of the trigger spring 308 and push these components in the distal position (cf. FIG. 7).

For dispensing a dose, the dial grip 71 is pressed by the user. It then disengages from the dial sleeve 60, and is rotationally constrained by the clicker teeth engagement between the tubular element 72 and the clicker 100. Axial movement of the dial grip 71 also causes the dial clicker 100 to be axially moved.

The drive sleeve is moved axially so that it disengages from its splined interface (cf. 45, 15) with the housing 3. The power reservoir 90 then causes the drive sleeve to rotate. Via the geared interface between the drive sleeve (41, 42) and the drive tube 43, the drive tube 43 is rotated which then drives the lead screw 30 through the housing into the bung 21. The drive sleeve causes the dial sleeve 60 to rotate, which causes the dose nut 50 to travel back towards the zero dose position.

Dispensing of a dose continues until the dose nut 50 reaches its zero dose abutment stop with the dial sleeve 60, or until the user releases the dial grip 71. When the zero dose abutment stop is engaged, torque from the power reservoir 90 is reacted via the dial sleeve 60 and dose nut into the housing 3. When the user releases the dial grip 71, the action of the trigger spring 308 acts to re-engage the splined interface between the drive sleeve and housing 3.

During dispense of a dose, the dial sleeve 60 and hence encoder disk 302 are rotating. Therefore, the optical encoder 302 is energised "awake" and reading the encoder disk 302. To differentiate between dialing and dose dispense, the dose assembly 304 also incorporates a mode switch comprising the mode contacts 307 between the clicker 100 and the dose assembly 304. The mode switch is a simple electrical switch triggered by axial travel of the clicker 100 when the dial grip 71 is depressed to dispense the dose. In FIG. 6, the mode switch is shown adjacent to the dose assembly 304. However it may be located anywhere on the device 200, wherein relative travel between components occurs during dose dispense but not during dose setting or vice-versa. At the end of dose, the dose assembly 304 may also emit a sound via the mentioned sounder to signal that the dose is complete, and/or additionally to provide further feedback after a predetermined dwell period.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Needle mounting feature
2 Needle detector
3 Housing
4 Movable feature
5 Outer surface
6 Needle unit
7 Needle hub
8 Cap
9 Recessed area
11 Main housing
12 Proximal housing
13 Cartridge holder
14 Window
20 Cartridge
30 Lead screw
40 Drive mechanism
41 Drive sleeve lower part
42 Drive sleeve upper part
43 Drive tube
44 Spline
50 Dose nut
60 Dial sleeve
71 Dial grip
72 Tubular element
90 Power reservoir
100 Clicker
101 Needle
200 Drug delivery device
301 Optical encoder
302 Encoder disk
303 Dial switch
304 Dose assembly
306 Carrier
307 Mode contact
308 Trigger spring
L1, L2 Lengths

The invention claimed is:

1. An assembly for a drug delivery device, the assembly comprising:
   a housing;
   a needle mounting feature;
   a needle detector movable with respect to the housing, the needle detector configured to detect whether a needle is mounted to the needle mounting feature;
   a movable feature movable with respect to the housing between a first position and a second position different from the first position, wherein the movable feature is configured to be in the second position when the needle is mounted to the needle mounting feature, and the movable feature is configured to be in the first position when the needle is not mounted to the needle mounting feature; and
   a cap configured to be secured to the assembly in a first mounting position when the movable feature is in the first position, and to be secured to the assembly in a second mounting position different from the first mounting position when the movable feature is in the second position, the cap configured to cover a distal end of the needle when the cap is in the second mounting position,
   wherein the needle detector is configured to trigger movement of the movable feature.

2. The assembly according to claim 1, wherein the movable feature is configured to move from the first position to the second position during mounting of the needle to the needle mounting feature.

3. The assembly according to claim 1, wherein the movable feature is configured to, in the second position, protrude from an outer surface of the housing, and to protrude, in the first position, from the outer surface of the housing less than the movable feature protrudes in the second position.

4. The assembly according to claim 1, wherein the assembly is configured to convert a movement of the needle detector into the movement of the movable feature.

5. The assembly according to claim 4, wherein the needle detector is configured to move in an axial direction, and wherein the movable feature is configured to move radially with respect to the axial direction responsive to the movement of the needle detector in the axial direction.

6. The assembly according to claim 1, wherein the movable feature comprises a face, and wherein the needle detector is configured to engage the face of the movable feature to move the movable feature when the needle detector is moved.

7. The assembly according to claim 1, wherein the movable feature is biased towards the first position.

8. The assembly according to claim 1 further comprising: a needle unit comprising the needle, wherein the needle unit is configured to be mounted to the needle mounting feature, and wherein the needle detector is configured to interact with the needle unit during mounting of the needle unit to the needle mounting feature, whereby the needle detector can detect whether the needle unit is mounted to the needle mounting feature.

9. The assembly according to claim 1, wherein the needle mounting feature is arranged in a recessed area of the housing.

10. The assembly according to claim 1, wherein the movable feature comprises a pin.

11. A drug delivery device comprising: an assembly comprising:
   a housing;
   a cartridge holder;
   a needle mounting feature; a needle detector movable with respect to the housing, the needle detector configured to detect whether a needle is mounted to the needle mounting feature;
   a movable feature movable with respect to the housing between a first position and a second position different from the first position, wherein the movable feature is configured to be in the second position when the needle is mounted to the needle mounting feature, and the movable feature is configured to be in the first position when the needle is not mounted to the needle mounting feature; and
   a cap configured to be secured to the assembly in a first mounting position when the movable feature is in the first position, and configured to be secured in a second mounting position different from the first mounting position when the movable feature is in the second position, the cap configured to cover a distal end of the needle when the cap is secured in the second mounting position,
   wherein the needle detector is configured to trigger movement of the movable feature.

12. The drug delivery device according to claim 11, wherein the cap is secured to the assembly either in the first mounting position or in the second mounting position, and wherein the cap covers the needle mounting feature and the needle detector.

13. The drug delivery device according to claim 11, wherein, when the cap is secured in the first mounting position, the drug delivery device comprises a first length and, when the cap is secured in the second mounting position, the drug delivery device comprises a second length, wherein the second length is greater than the first length.

14. The drug delivery device according to claim 11, wherein the movable feature is configured to prevent the cap from being secured in the first mounting position when the movable feature is in the second position.

15. The drug delivery device according to claim 11, wherein, when the cap is secured in the second mounting position, a dose indicator of the drug delivery device is visible for a user, and when the cap is secured in the first mounting position, the dose indicator is not visible for the user.

16. The drug delivery device according to claim 11, further comprising: a cartridge mounted to the cartridge holder, the cartridge configured to retain a drug; and a drive mechanism configured to dispense the drug from the cartridge, wherein the drive mechanism comprises a piston rod.

17. The drug delivery device according to claim 16, wherein the drug comprises a pharmaceutically active compound.

18. An assembly for a drug delivery device, the assembly comprising:
   a needle mounting feature;
   a needle detector configured to detect whether a needle is mounted to the needle mounting feature;
   a housing; and
   a movable feature movable with respect to the housing between a first position and a second position different from the first position, wherein the movable feature is configured to be in the second position when the needle is mounted to the needle mounting feature, and the movable feature is configured to be in the first position when the needle is not mounted to the needle mounting feature,
   wherein the needle detector is movable with respect to the housing, and wherein the needle detector is configured to trigger movement of the movable feature, and
   wherein the movable feature comprises a face which is spaced from the needle detector when the movable feature is in the first position, and wherein the needle detector is configured to engage the face of the movable feature to move the movable feature when the needle detector is moved.

* * * * *